(12) United States Patent
Trdič et al.

(10) Patent No.: US 9,797,845 B2
(45) Date of Patent: Oct. 24, 2017

(54) APPARATUS AND METHOD FOR MONITORING MELT STREAM WITHIN A FIBERIZING APPARATUS

(71) Applicant: IZOTEH D.O.O., Ljubljana-Črnuče (SI)

(72) Inventors: Francelj Trdič, Ljubljana-Črnuče (SI); Miha Trdič, Ljubljana-Črnuče (SI)

(*) Notice: Subject to any disclaimer, the term of this patent is extended or adjusted under 35 U.S.C. 154(b) by 0 days.

(21) Appl. No.: 14/906,751

(22) PCT Filed: Sep. 20, 2013

(86) PCT No.: PCT/SI2013/000055
§ 371 (c)(1),
(2) Date: Jan. 21, 2016

(87) PCT Pub. No.: WO2015/041611
PCT Pub. Date: Mar. 26, 2015

(65) Prior Publication Data
US 2016/0161419 A1    Jun. 9, 2016

(51) Int. Cl.
*G01N 21/85* (2006.01)
*C03B 37/05* (2006.01)
(Continued)

(52) U.S. Cl.
CPC ........... *G01N 21/85* (2013.01); *C03B 37/055* (2013.01); *C03B 37/07* (2013.01); *G01N 11/00* (2013.01)

(58) Field of Classification Search
CPC .. G01N 11/00; G01N 11/02; G01N 2011/006; G01N 2011/008; G01N 21/89;
(Continued)

(56) References Cited

U.S. PATENT DOCUMENTS 5,116,397 A * 5/1992 Nurmi ................... C03B 37/055
65/517
5,131,935 A * 7/1992 Debouzie .............. C03B 37/055
65/456
(Continued)

FOREIGN PATENT DOCUMENTS

| EP | 1409423 | 6/2006 |
| EP | 217484 | 4/2010 |
| WO | WO9942413 | 8/1999 |

OTHER PUBLICATIONS

PCT Search Report for PCT/SI2013/000055, dated Jun. 23, 2004.

*Primary Examiner* — John Lee
(74) *Attorney, Agent, or Firm* — Robert Platt Bell

(57) ABSTRACT

This invention addresses technical problem of optimizing output of a melt cascade, which is used in production of mineral fiber (so called mineral wool as known in state of the art being stone wool, slag wool or other type of mineral wool). These technical problems are solved by steps of determining (a) trajectory of movement of a melt stream, (b) melt concentration relative to surrounding air between the first and the second rotating wheels, and (c) movement vector, and further by regulating of movement of melt stream (i.e., drop mass), said regulation mostly achieved through variation in point of contact of melt and rotating wheel or plurality thereof. This is achieved by determining three key parameters: (a) trajectory of movement of melt stream, (b) melt concentration relative to surrounding air between the first and the second rotating wheels, and (c) movement vector, and further by analyzing these three key.

10 Claims, 5 Drawing Sheets

(51) Int. Cl.
*C03B 37/07* (2006.01)
*G01N 11/00* (2006.01)

(58) Field of Classification Search
CPC ........... G01N 21/8901; G01N 21/8903; G01N 21/85; C03B 37/055; C03B 37/05; C03B 37/07

See application file for complete search history.

(56) References Cited

U.S. PATENT DOCUMENTS

| | | | | |
|---|---|---|---|---|
| 5,987,927 | A * | 11/1999 | Melinand | C03B 37/055 65/164 |
| 6,202,448 | B1 * | 3/2001 | Melinand | C03B 37/055 65/377 |
| 2013/0280979 | A1 * | 10/2013 | McKee | D01F 2/00 442/392 |
| 2016/0161419 | A1 * | 6/2016 | Trdic | C03B 37/055 250/573 |

* cited by examiner

US 9,797,845 B2

APPARATUS AND METHOD FOR MONITORING MELT STREAM WITHIN A FIBERIZING APPARATUS

CROSS-REFERENCE TO RELATED APPLICATIONS

The present application is a §371 National Stage Application of PCT/SI2013/000055 filed on, Sep. 20, 2013 which is incorporated herein by reference.

FIELD OF THE INVENTION

This invention addresses technical problem monitoring characteristics of a melt cascade (for purposes of this invention this term describing melt in either droplets, or streams, or rivulets, or other type of flow cascading from a furnace or like through a melt vessel, and onto a rotating wheel or plurality thereof, and between said rotating wheels) which is formed in production of mineral fiber (so called mineral wool as known in state of the art being stone wool slag wool or other type of mineral wool). This production comprises mainly of pouring of melt, preferably in form of a jet or a stream, said melt comprising material to be solidified into fiber, onto said rotating wheels (in state of the art also known as rotors) comprising of a first rotating wheel where melt is to be solidified (at least in part) in form of fibers which are blown off said rotating wheel, remainder to be passed to the second rotating wheel and thrown back onto the first rotating wheel and to third rotating wheel and so forth (of course assuming that there are more than one rotating wheel). In addition to monitoring, the technical problem solved by the present invention is also to ascertain where the production is performed with at least waste as possible.

BACKGROUND OF THE INVENTION

A typical fiberizing apparatus in state of the art is described in European Patent Specification EP1409423, published Apr. 21, 2004. A typical spinning machine consists of 3 to 4 fiberizing rotating wheels, also known as the spinning wheels, or rotating wheels (a term used in this patent application), or rotors.

The mineral melt discharged from the melting furnace or similar device for heating up and melting raw materials used in mineral wool formation forms a nearly vertical melt stream as it is poured onto the spinning machine. The melt stream is directed towards the mantle surface of the first wheel where it partly adheres to the surface, is drawn in motion and forms a melt film. A part of the melt forms, with the aid of the centrifugal force, liquid ligaments solidify to the mineral wool fibers while the remaining quantity of the melt is thrown out as a cascade of drops against the mantle surface of the adjacent second wheel in the series. Again, a part of the melt adheres to the second wheel surface sufficiently to be formed into fibers and the remainder is thrown onto the mantle surface of the third wheel of the spinner machine and so forth, until the last wheel where the remaining mass flow of the melt is assumed to be low enough to fiberize completely.

Binder may be applied on the formed mineral fibers, either during fiber formation or afterwards, in form of a droplet spray. The mineral fibers formed on the wheels of the spinning machine are transported away from the point of origin on the melt film, initially in the radial direction due to the centrifugal force. As the fibers enter the zone of the coaxial air flow generated by the spinning machine fan, i.e., the blow-in flow, they are drawn in a predominantly axial motion and transported to the collecting chamber where the primary layer of the mineral wool is formed.

None of patents searched showed any monitoring method or means.

BRIEF SUMMARY OF THE INVENTION

Fiber formation is achieved through competing centrifugal force and air entrainment force by virtue of air blowing onto the rotating wheel on one side, and viscous and surface tension forces keeping melt film to the rotating wheel on another side. When former exceeds latter the melt is lifted from the rotating wheel, the droplets are elongated until they stretch and solidify in form of a fiber. The process may vary from this description, however, this does not alter the essence of this invention as described below.

For purposes of this application progression of melt from one rotating wheel to another is called melt cascading.

A method and apparatus for monitoring melt stream within a fiberizing apparatus solves the above referenced technical problem by steps of determining: (a) trajectory of movement of melt stream, (b) melt concentration relative to surrounding air between the first and the second rotating wheels, and (c) movement vector. This method provides for contactless evaluation of movement of the melt stream, and the result could be used for regulation of the impingement point between the melt stream and the first rotating wheel which in turn enables operation within an optimum regime according to this invention.

The optimum regime in accordance with this invention is governed by a compromise between minimum fraction of solidified shots, (i.e., parts of the melt which are not transformed into fiber, and freeze during this process) and production yield on other hand. This regime can be observed in FIG. 6, and is signified by an arrow—of course, in a real-life application, and also claimed by this patent application is area to the left and to the right to the arrow's point. The optimum regime (31 in FIG. 6) is approximately bound by (34) as a minimum angle of the impingement point between the melt stream and the first rotating wheel (7), and (35) as maximum angle of the impingement point between the melt stream and the first rotating wheel (7).

The apparatus according to this invention comprises a monitoring means, and means for evaluating the melt cascade features. The monitoring means comprises at least a camera operating within visual part of a light spectrum, and a data acquisition means known in the state of the art for recognizing intensity of light (intensity of luminance) emitted from the melt cascading.

The steps comprising the method according to this invention may also include direction, position, and velocity of movement of the melt cascade, said melt predominantly in form of droplets, and further, information on the position of melt film on the rotating wheel or plurality thereof.

Regulation as a result of this invention therefore depends on the trajectory of the movement of the melt cascade, concentration of the melt between the first and the second rotating wheel, and the movement vector (i.e., velocity) of said melt cascade.

For purposes of this application the term "spinning rotating wheel" is also referred to simply as a "rotating wheel". For purposes of this application, and unless explicitly noted otherwise, the words left, right, up, down, vertical, horizontal, forward, backward do not mean strict expressions but rather they should be understood as essentially, or approximately left, right, up, down, horizontal, vertical, forward, and backward and they should be interpreted as these expressions would be understood by one skilled in the art.

BRIEF DESCRIPTION OF THE SEVERAL VIEWS OF THE DRAWINGS

The foregoing aspects and many additional advantages of this invention will become more readily appreciated by reference to the following detailed description, below, when taken in conjunction with the accompanying drawings, all forming part of this patent application, wherein.

DETAILED DESCRIPTION OF THE INVENTION

It should be immediately presented that scope of this invention is not limited by number of rotating wheels. For purposes of this invention it is sufficient if the fiberizing apparatus has at least one rotating wheel, preferably two rotating wheels. Four rotating wheels are presented as such apparata are known in the art, and as the principles can be explained better with four rotating wheels. It should further be noted that it is also possible for this invention to function to have only three wheels thus rendering the fourth rotating wheel unnecessary for purposes of this application. Further, more than four rotating wheels can be used. However, most common setup seems to be that of four wheels therefore the invention is described with this setup but this should not be seen as a limiting factor as two, three, four, five or more rotating wheels in a fiberizing apparatus (also known as "spinning machine") are both possible, and viable, depending on other factors comprising one or more characteristics such as (for informative purposes only) viscosity, density, mineralogical setup or other characteristics of melt, and/or minimum distance, rotational speed, material of rotating wheels or other characteristics of a device.

Figure 1:
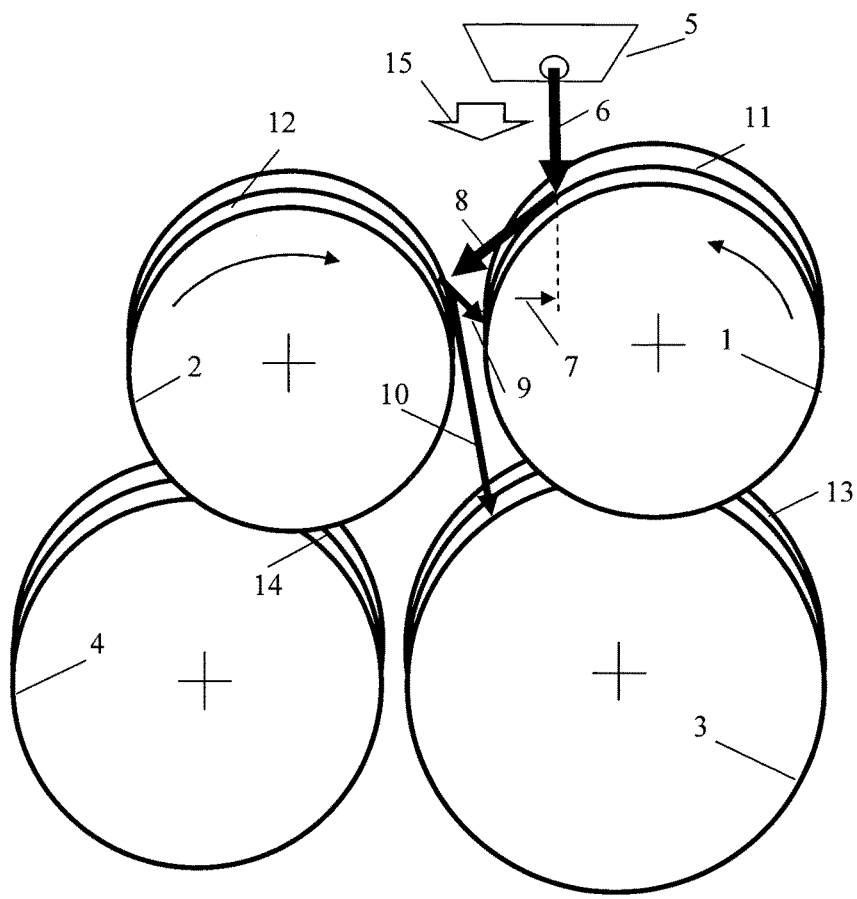
FIG. 1 shows the first rotating wheel (1), the second rotating wheel (2), the third rotating wheel (3), the fourth rotating wheel (4), melt container (5), the melt stream onto the first rotating wheel (6), the impingement point between melt stream and the first rotating wheel (7), the melt stream from the first rotating wheel onto the second rotating wheel (8), the melt stream deflecting from the second rotating wheel onto the first rotating wheel (9), the melt stream from the second rotating wheel toward a space in-between the third and the fourth rotating wheels (10), a film on the first rotating wheel (11), a film on the second rotating wheel (12), a film on the third rotating wheel (13), a film on the fourth rotating wheel (14), and the direction of blowing air (15).
Figure 2:
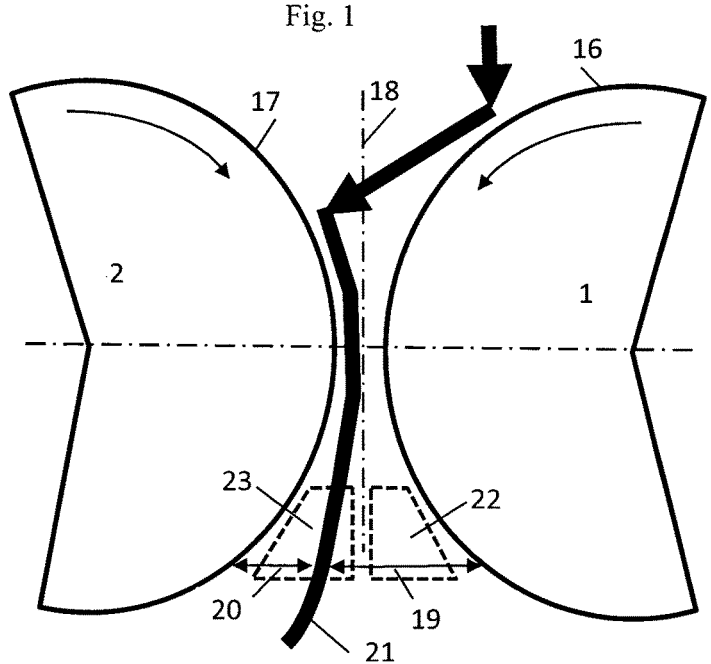
FIG. 2 shows an edge of the first rotating wheel (16), an edge of the second rotating wheel (17), the geometric center between the first and the second rotating wheel (18), the distance between a center of a melt trajectory to the edge of the first rotating wheel (19), the distance between the center of the melt trajectory to the edge of the second rotating wheel (20), the melt trajectory (21), an area for luminance detection for the first rotating wheel component (22), and an area for luminance detection for the second rotating wheel component (23).
Figure 3:
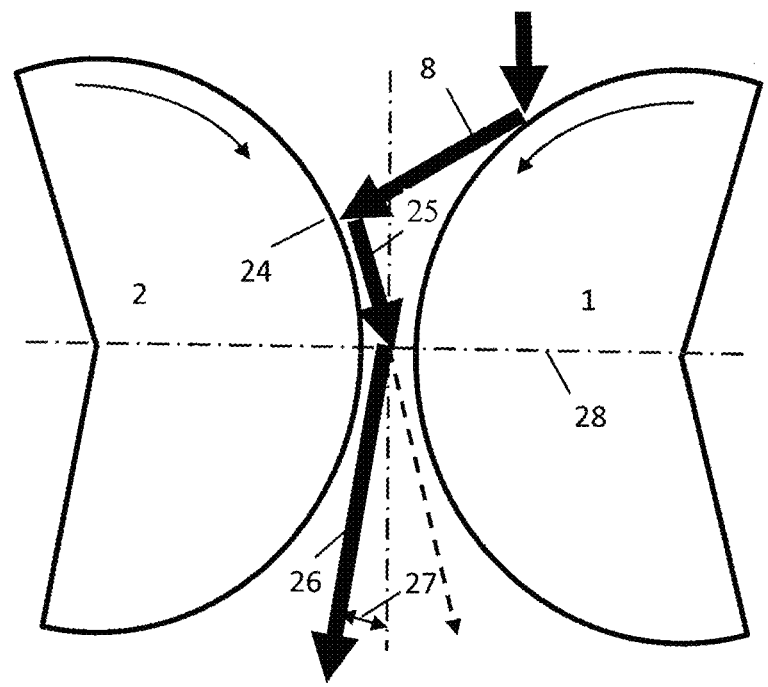
FIG. 3 shows the first rotating wheel (1), the second rotating wheel (2), the melt stream from the first rotating wheel onto the second rotating wheel (8), the impingement point between melt stream and the second rotating wheel (24), the melt stream from the second rotating wheel into an area between the wheels above the axis connecting the center points of the first and the second rotating wheels (25), the melt stream from the second rotating wheel into an area between the wheels below the axis connecting the center points of the first and the second rotating wheels (26), a vector of melt movements below connecting the centers of the first and the second rotating wheels (27), and an axis connecting the centers of the first and the second rotating wheels (28).
Figure 4:
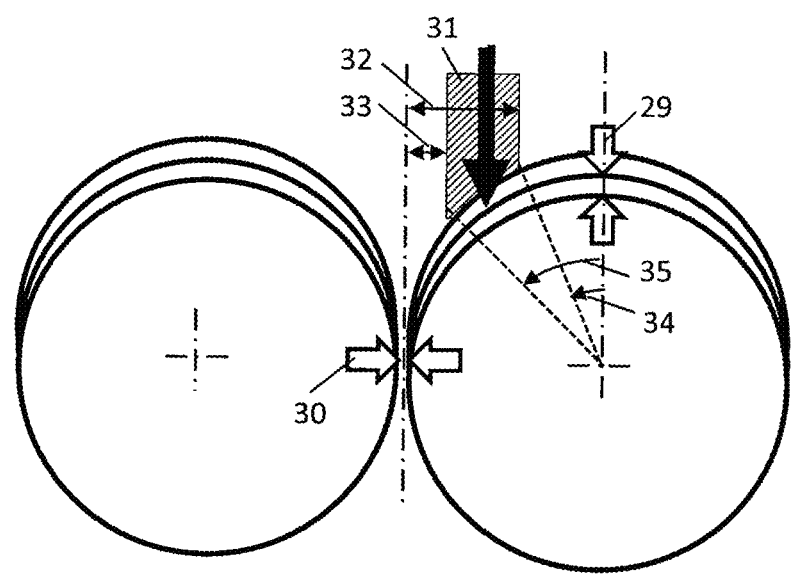
FIG. 4 shows a vertical reference (29), a horizontal reference (30), an area of melt stream inflow (31), the far right position of melt stream inflow related to geometric center between the first and the second rotating wheel (32), the far left position of melt stream inflow related to geometric center between the first and the second rotating wheel (33), the far right position of melt stream inflow regarding an angle with respect to vertical axis of the first rotating wheel (34), and the far left position of melt stream inflow regarding an angle with respect to vertical axis of the first rotating wheel (35).
Figure 5:
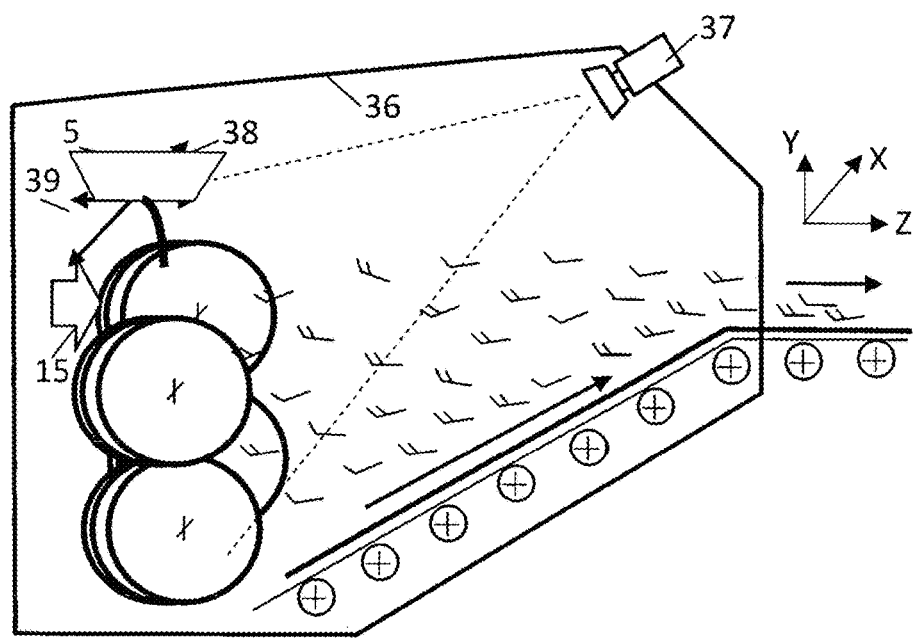
FIG. 5 shows a collecting chamber (36), camera (37), the direction of the melt container positioning left/right (38), and the direction of the melt container positioning forward/backward (39).

Referring to FIG. 1, in one embodiment of the present invention, the melt (6) coming into contact with the first rotating wheel (1) is partially comprising a film (11) primarily as a result of viscous forces and surface tension. The remainder of the melt is transported onto the second rotating wheel (2) preferably in form of melt stream (8). Part of this melt again forms a melt film (12) on the second rotating wheel (2), another part forms a melt stream (10) flowing between the first (1) and the second (2) rotating wheel, and the remainder (9) is thrown back into the first rotating wheel (1).

Space between both rotating wheels (3) and (4) is filled with part of the melt from rotating wheel (2), part of the melt from rotating wheel (1) and part of the melt which has passed in between both rotating wheels (1) and (2). It should be noted that rotating wheels (3) and (4) are not necessary for carrying out this invention, and that melt cascade with only rotating wheels (1) and (2) is possible (so called two wheel fiberizing apparata as known in state of the art). Further, part of film (11) from perimeter of rotating wheel (1) and part of film (12) from perimeter of rotating wheel (2) is transported to rotating wheels (3) and (4) as a consequence of centrifugal force acting on films (11), and (12), respectively.

In the axial direction (meaning the direction essentially normal to the plane in which the first rotating wheel essentially rotates, or a direction essentially co-linear to the axis of the first rotating wheel), the velocity of blowing air (15) is acting on the film. It should be immediately mentioned that this direction is not limiting for this invention, and that the air (which represents a blowing or blow-off means) may blow in any desired direction, including essentially within the plane in which the first rotating wheel essentially rotates). This air is aiming to entrain the melt (usually in form of droplets) and blow it off the rotating wheel. When total force of air flow and centrifugal component acting on the film overcomes viscous and surface tension components as well as possible forces keeping the film on said rotating wheels, the film is gradually deformed, and a droplet formed. This droplet is entrained by airflow, and elongated in direction of the air flow force and the centrifugal force resultant. The droplet is therefore transformed into a fiber, which is even more elongated until it solidifies and falls in the collecting chamber or other device for collecting this fiber or plurality thereof.

The quality of fiber formation is dependent on distribution of melt concentration on different wheels, and this concentration, in turn, depends on cascade movement of melt mass (8), (9), and (10). This, in turn, depends on melt stream (6) contact characteristics with the first rotating wheel (1), especially the impingement point (7).

Figure 7:
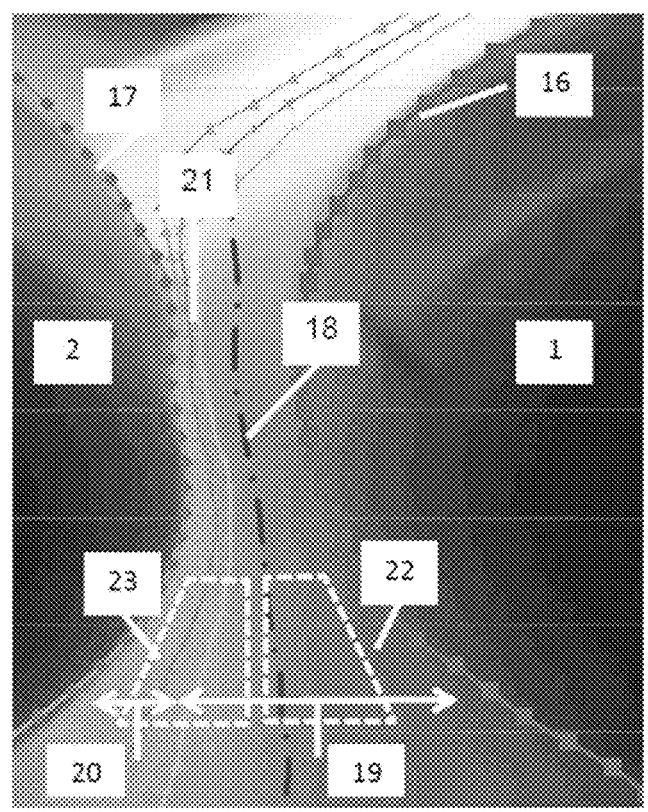
FIG. 7 is presented for better understanding of the reader, and is a photograph from an actual experiment, which has been for purposes of this application been redrawn in FIG. 2.
Figure 8:
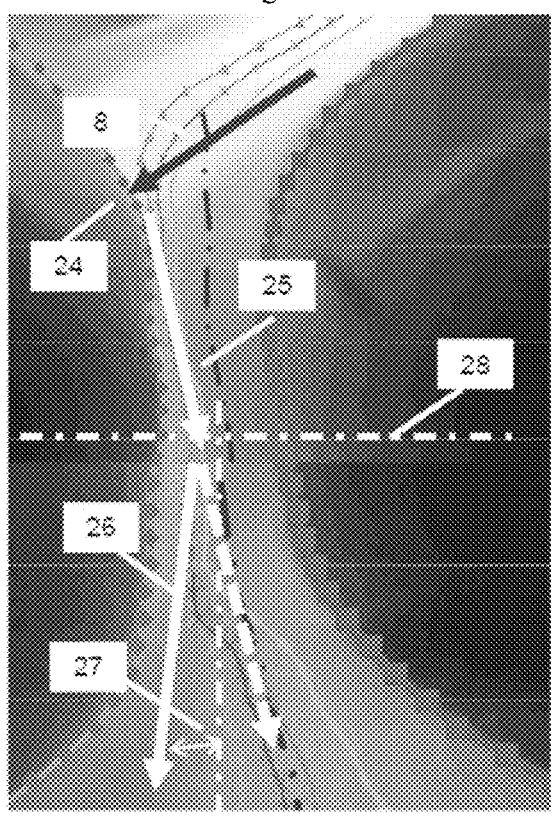
FIG. 8 is presented for better understanding of the reader, and is photograph from an actual experiment, which has been for purposes of this application been redrawn in FIG. 3.
Figure 9:
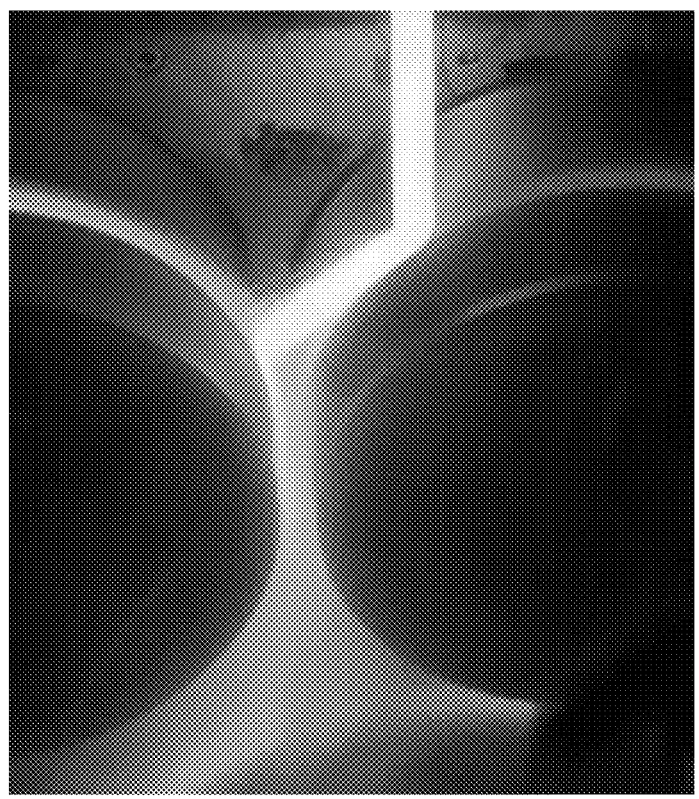
FIG. 9 is presented for better understanding of the reader, and is a photograph from actual experiment, which has been for purposes of this application redrawn in FIG. 4.

In order to prove this, several tests were performed, images of which are also presented in FIGS. 7 through 9 in this patent application.

The impingement point for purposes of this application means the approximate center of the melt stream inflow impact position. Such a center cannot be determined with large degree of accuracy, so it should be interpreted having in mind one skilled in the art. Hence, any reference to impingement point should be interpreted likewise, (i.e., approximate reference to approximate center of the melt stream inflow impact position.)

Figure 6:
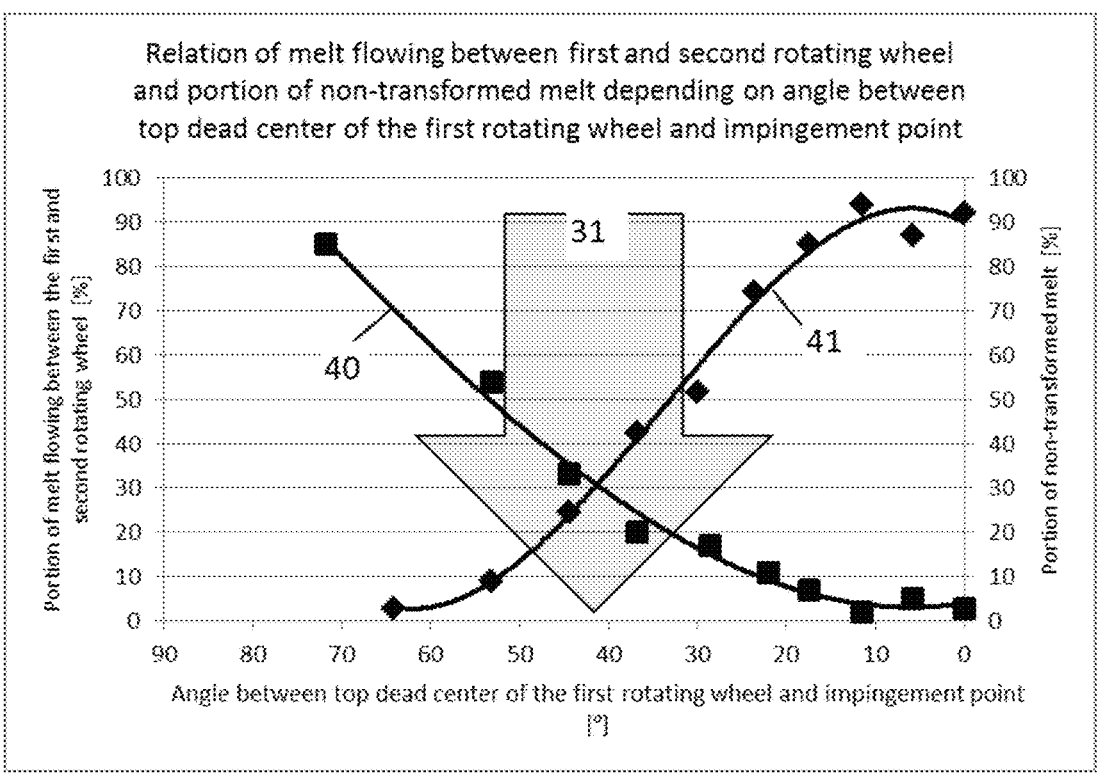
FIG. 6 shows the area of the melt stream inflow (31), a portion of the melt flowing between the first and the second rotating wheel with respect to melt stream inflow position (40), a portion of and a formation of non-fiberized material with respect to the melt stream inflow position (41).

The results of tests are presented in form of a graph in FIG. 6.

The abscissa in FIG. 6 shows the position of impingement point between the melt stream and the first rotating wheel, expressed in degrees. 0° means that the impingement point is approximately in top dead center of the first rotating wheel. 90° means that the approximate center of the melt stream inflow misses the first rotating wheel and falls in space between the first and the second rotating wheel. Both curves present quality (in terms of shot content), and quantity (in terms of fibers) depending on the angle between top dead center of the first rotating wheel and impingement point (7). Curve (40) in FIG. 6 presents quantity of melt in % which passes between the first and the second rotating wheels, and the difference to 100% is the percentage of melt which is in contact with both the first and the second rotating wheels. Curve (41) in FIG. 6 presents the ratio between actual shot content and maximum shot content at impingement point 0° [%]. These shots are also considered waste for purposes of this patent application, hence, minimization of shots is one of goals of this application. The other goal is also to minimize the amount of non-transformed melt material, and in order to be able to do this, the novel monitoring and/or regulation method and apparatus are proposed herein.

The ordinate in FIG. 6 on the left shows the portion of melt flowing between the first and the second rotating wheel with respect to the melt stream inflow position (40), the ordinate in FIG. 6 on the right shows portion of formation of the non-transformed melt (nonfiberized) material with respect to melt stream inflow position (41). From this graph it is evident that the optimum operating point (to address one of technical problems of this invention) is where both curves (40) and (41) intersect.

The subject of this invention is therefore a method by which determination of impingement point between melt stream and the first rotating wheel (7) is performed in such a way that three key parameters are determined: (a) trajectory of movement of melt stream, (b) melt concentration relative to surrounding air between the first and the second rotating wheels, and (c) movement vector.

The apparatus should therefore possess the means for (a) determining the impingement point between the melt stream and the first rotating wheel (7) based on the solidified percentage of shots and production yield, and (b) comparing said impingement point between the melt stream and the first rotating wheel (7) with an optimum operating range, and further this apparatus should posses a regulation system connected to said apparatus for ensuring that said impingement point between melt stream and the first rotating wheel (7) is within optimum operating range.

The apparatus should therefore further possess the means for determining (a) the trajectory of movement of the melt stream, (b) the melt concentration relative to surrounding air between the first and the second rotating wheels, and (c) the movement vector and analytical system connected thereto.

In one embodiment of this invention these objectives are met by an apparatus for monitoring and regulating melt stream (which can be even in the predominant form of droplets) movement. The apparatus is comprised of two parts: a part for monitoring (optionally comprising evaluation of process), and part for regulating, which is carried out by regulation of the impingement point between the melt stream and the first rotating wheel (7).

The apparatus for monitoring comprises a camera (37) which can be any type of digital camera, preferably (due to price) operating within visual spectrum, however, any spectrum (including IR, for different reasons) is possible. Said camera (37) is set up in a general axial position relative to the rotating wheels on the upper part of collecting chamber (36). This position enables camera (37) to capture an image or plurality thereof of the melt stream movement and in-depth information on film position on the relevant rotating wheels as well as the impingement point between the melt stream and the first rotating wheel (7). A preferred position of camera is 25° to 50° relative to the first rotating wheel axis which permits capturing in-depth information on vertical reference (29).

The captured image or plurality thereof is analyzed by means of image processing on a computerized system in real time taking advantage of three key parameters measured by present apparatus, and method: (a) trajectory of movement of the melt stream, (b) melt concentration relative to surrounding air between the first and the second rotating wheels, and (c) movement vector.

The trajectory of movement of the melt stream according to this invention is connected to intensity of luminance of said melt. The higher the intensity, the larger the concentration. Following the highest points of intensity (luminance) within the same monitoring window (region of interest), and connecting said highest points results in the melt trajectory (21).

A parameter of a horizontal trajectory point is determined as a difference between a detected melt trajectory (21), and the geometric center between the first and the second rotating wheels (18) which is determined relative to an edge of the first rotating wheel (16), and an edge of the second rotating wheel (17). Deviation of said trajectory (21) from the edge of the first rotating wheel (16) is given by a distance between a center of a melt trajectory to the edge of the first rotating wheel (19), and the deviation of said trajectory (21)

from the edge of the second rotating wheel (17) is given by a distance between the center of the melt trajectory to the edge of the second rotating wheel (20).

The integral parameter of trajectory (21) is, in this invention, defined as an average value of a set of vertical points between said trajectory (21) and the geometric center between the first and the second rotating wheels (18), vertical from an impingement point between the melt stream and the second rotating wheel (24) to the upper level of the third rotating wheel (in case of a fiberizing apparatus with three rotating wheels), or the third and the fourth rotating wheels (in case of a fiberizing apparatus with four or more rotating wheels), or to some predetermined position (incase of a fiberizing apparatus with two rotating wheels).

A further parameter which needs to be determined is distribution of concentration. This distribution is determined by calculation of integral value of luminance in the area for luminance detection for the first rotating wheel component (22) and in the area for luminance detection for the second rotating wheel component (23), both in the space between the rotating wheels, and normalized to a reference value presented by the area of the first rotating wheel (1) for the first rotating wheel (1), and the area of the second rotating wheel (2) for the second rotating wheel (2). The border between the first (1), and the second (2) rotating wheels is determined as geometric center between the first and the second rotating wheel (18).

A further parameter to be determined is the movement vector. This vector describes movement of a plurality of the melt, and can therefore be regarded as analogous to lumped parameter modeling analysis. There are two vectors given: the first for the upper part, and the second for the lower part. The former is the vector for the melt stream from the second rotating wheel into an area between the wheels above the axis connecting the center points of the first and the second rotating wheels (25) while the latter is the vector for the melt stream from the second rotating wheel into an area between the wheels below the axis connecting the center points of the first and the second rotating wheels (26).

The first vector is defined as a detected value in the direction of tangential component of the melt stream from the first rotating wheel onto the second rotating wheel (8) in the impingement point between the melt stream and the second rotating wheel (24) to the axis connecting the centers of the first and the second rotating wheels (28). The second vector is defined below the axis connecting the centers of the first and the second rotating wheels (28), and its direction is defined by the vector of melt movements below the axis connecting the centers of the first and the second rotating wheels (27).

Further parameters to be taken into consideration are reference values. The camera (37) is capturing the image which is a projection of 3D onto 2D. The position of the melt stream therefore varies due to freezing of the melt, changing thermodynamic properties, and camera vibrations (as observed as a consequence of collection chamber vibrations). This is a problem which is addressed by setting up the reference areas to which other spatial and luminance analyses are referenced to.

The vertical reference (29) is detected as the film position on the first rotating wheel. Due to the angular position of camera (37) triangulation is used to calculate the in-depth position of the stream. The horizontal reference (30) is the position between the first rotating wheel and the second rotating wheel where the distance between the first rotating wheel and the second rotating wheel is the minimum.

A further step to be determined is an elimination of noise (interfering values). Lumps of non-fiberized material (non-transformed melt) are interfering with data acquisition. To eliminate their influence, the program performs dynamic analysis in short time intervals. Elimination of interference is achieved by attributes of non-validity of detection in areas of luminance with high frequency.

Having determined all steps necessary for carrying out this invention so far, the following technological parameters of operation were identified:
  (a) the average relative trajectory (21) position is less than 40% the minimum distance in a vertical direction varying from the impingement point between melt stream and the second rotating wheel (24) to the axis of the first and the second rotating wheels (28);
  (b) the luminance intensity in the area for luminance detection for the second rotating wheel component (23) is at least 45% of luminance sum in the area (23) and (22), where (22) is the area for luminance detection for the first rotating wheel component in lower space between the rotating wheels, i.e., from the axis of of the first and the second rotating wheels (28) generally in downward direction to lower edge of the first or the second rotating wheels, respectively, i.e., from the axis of the first and the second rotating wheels (28) generally in downward direction to lower edge of the first and the second rotating wheels.
  (c) the direction of the vector of melt movements below axis of the first and the second rotating wheels (27) of the melt stream from the second rotating wheel into area between the wheels below axis of the first and the second rotating wheels (26) in the lower space between the rotating wheels is less than +15°, where 0° stands for vertical direction downward, and positive direction is counterclockwise direction.

While the preferred embodiment and various alternative embodiments of the invention have been disclosed and described in detail herein, it may be apparent to those skilled in the art that various changes in form and detail may be made therein without departing from the spirit and scope thereof.

The invention claimed is:

1. A method for monitoring a melt stream within a fiberizing apparatus comprising at least a first rotating wheel and a second rotating wheel, for forming of a mineral melt into fibers comprised of the following steps:
  determining a melt concentration relative to surrounding air between the first rotating wheel and the second rotating wheel;
  determining a trajectory of movement of said melt stream; and
  determining at least one movement vector of said melt stream, the at least one movement vector comprising at least one vector representing direction and velocity of at least a portion of the melt stream.

2. The method for monitoring a melt stream within a fiberizing apparatus according to claim 1, wherein said determination of melt concentration is comprised of the following steps:
  determining a first integral value of luminance in an area for luminance detection for a component of the first rotating wheel (22),
  determining a second integral value of luminance in an area for luminance detection for a component of the second rotating wheel (23),
  normalizing the first integral value and the second integral value to a reference value presented by an area of the first rotating wheel (1) for the first rotating wheel (1), and the area of the second rotating wheel (2) for the second rotating wheel (2), wherein a border between the first rotating wheel (1), and the second rotating wheel (2) is determined as a geometric center (18) between the first rotating wheel (1) and the second rotating wheel (2).

3. The method for monitoring a melt stream within a fiberizing apparatus according to claim 1, wherein said determination of trajectory of movement of said melt stream is comprised of connecting points of essentially a highest luminance (21) within a monitoring window.

4. The method for monitoring melt stream within a fiberizing apparatus according to claim 1, wherein said at least one movement vector is comprised of two vectors:
   a first vector (25) for said melt stream from the second rotating wheel into an area between the first rotating wheel and second rotating wheel above an axis (28) connecting center points of the first rotating wheel (1) and the second rotating wheel (2), said first vector comprised of a detected velocity value in a direction of a tangential component (8) of the melt stream from the first rotating wheel (1) onto the second rotating wheel (2) in an impingement point (24) between the melt stream and the second rotating wheel (2) to an axis (28) connecting the centers of the first rotating wheel (1) and the second rotating wheel (2),
   a second vector (26) for said melt stream from the second rotating wheel (2) into an area between the first rotating wheel (1) and the second rotating wheel (2) below the axis (28) connecting the center points of the first rotating wheel (1) and the second rotating wheel (2), said second vector having a direction (27) comprised of a vector of melt movements below the axis (28) connecting the centers of the first rotating wheel and the second rotating wheel.

5. An apparatus for monitoring a melt stream within a fiberizing apparatus including at least a first rotating wheel and a second rotating wheel, the apparatus for monitoring comprising:
   means for determining trajectory of movement of the melt stream,
   means for determining melt concentration relative to surrounding air between the first rotating wheel and the second rotating wheel, and
   means for determining the at least one movement vector and analytical system connected thereto for determining an optimum impingement point (7) between the melt stream and the first rotating wheel, the at least one movement vector comprising at least one vector representing direction and velocity of at least a portion of the melt stream.

6. Apparatus for monitoring melt stream within a fiberizing apparatus according to claim 5, further comprising:
   a monitor monitoring of portions of the melt stream passing through a space between said first rotating wheel (1) and said second rotating wheel (2),
   a melt stream evaluator determining distribution of said melt, and regulating movement of said melt stream by varying point of contact of the melt with the first rotating wheel and the second rotating wheel,
   wherein said monitor is comprised at least of a camera operating within a visual part of a light spectrum, and a data acquisition system recognizing luminance from the camera connected thereto.

7. The method for monitoring melt stream within a fiberizing apparatus according to claim 2, wherein said determination of trajectory of movement of said melt stream comprises connecting points of essentially a highest luminance (21) within a monitoring window.

8. The method for monitoring melt stream within a fiberizing apparatus according to claim 2, wherein said at least one movement vector is comprised of two vectors:
   a first vector (25) for said melt stream from the second rotating wheel into an area between the first rotating wheel and second rotating wheel above an axis (28) connecting center points of the first rotating wheel (1) and the second rotating wheel (2), said first vector comprised of a detected velocity value in a direction of a tangential component (8) of the melt stream from the first rotating wheel (1) onto the second rotating wheel (2) in an impingement point (24) between the melt stream and the second rotating wheel (2) to an axis (28) connecting the centers of the first rotating wheel (1) and the second rotating wheel (2),
   a second vector (26) for said melt stream from the second rotating wheel (2) into an area between the first rotating wheel (1) and the second rotating wheel (2) below the axis (28) connecting the center points of the first rotating wheel (1) and the second rotating wheel (2), said second vector having a direction (27) comprised of a vector of melt movements below the axis (28) connecting the centers of the first rotating wheel and the second rotating wheel.

9. The method for monitoring melt stream within a fiberizing apparatus according to claim 3, wherein said at least one movement vector is comprised of two vectors:
   a first vector (25) for said melt stream from the second rotating wheel into an area between the first rotating wheel and second rotating wheel above an axis (28) connecting center points of the first rotating wheel (1) and the second rotating wheel (2), said first vector comprised of a detected velocity value in a direction of a tangential component (8) of the melt stream from the first rotating wheel (1) onto the second rotating wheel (2) in an impingement point (24) between the melt stream and the second rotating wheel (2) to an axis (28) connecting the centers of the first rotating wheel (1) and the second rotating wheel (2),
   a second vector (26) for said melt stream from the second rotating wheel (2) into an area between the first rotating wheel (1) and the second rotating wheel (2) below the axis (28) connecting the center points of the first rotating wheel (1) and the second rotating wheel (2), said second vector having a direction (27) comprised of a vector of melt movements below the axis (28) connecting the centers of the first rotating wheel and the second rotating wheel.

10. The method for monitoring melt stream within a fiberizing apparatus according to claim 7, wherein said at least one movement vector is comprised of two vectors:
   a first vector (25) for said melt stream from the second rotating wheel into an area between the first rotating wheel and second rotating wheel above an axis (28) connecting center points of the first rotating wheel (1) and the second rotating wheel (2), said first vector comprised of a detected velocity value in a direction of a tangential component (8) of the melt stream from the first rotating wheel (1) onto the second rotating wheel (2) in an impingement point (24) between the melt stream and the second rotating wheel (2) to an axis (28) connecting the centers of the first rotating wheel (1) and the second rotating wheel (2), a second vector (26) for said melt stream from the second rotating wheel (2) into an area between the first rotating wheel (1) and the second rotating wheel (2) below the axis (28) connecting the center points of the first rotating wheel (1) and the second rotating wheel (2), said second vector having a direction (27) comprised of a vector of melt movements below the axis (28) connecting the centers of the first rotating wheel and the second rotating wheel.

\* \* \* \* \*